United States Patent [19]

Merger et al.

[11] Patent Number: 5,166,443
[45] Date of Patent: Nov. 24, 1992

[54] PREPARATION OF 2,2-DISUBSTITUTED PENTANE-1,5-DIAMINES

[75] Inventors: Franz Merger, Frankenthal; Claus-Ulrich Priester; Tom Witzel, both of Ludwigshafen; Gerhard Koppenhoefer, Roemerberg; Ludwig Schuster, Limburgerhof, all of Fed. Rep. of Germany

[73] Assignee: BASF Aktiengesellschaft, Ludwigshafen, Fed. Rep. of Germany

[21] Appl. No.: 676,086

[22] Filed: Mar. 17, 1991

[30] Foreign Application Priority Data

Mar. 30, 1990 [DE] Fed. Rep. of Germany ....... 4010252
Jul. 7, 1990 [DE] Fed. Rep. of Germany ....... 4021726
Feb. 28, 1991 [DE] Fed. Rep. of Germany ....... 4106340

[51] Int. Cl.$^5$ ............................................ C07C 209/48
[52] U.S. Cl. ..................... 564/473; 564/471; 564/472; 564/446; 564/489; 564/490
[58] Field of Search ............... 564/473, 490, 446, 453, 564/448, 454, 471, 472

[56] References Cited

U.S. PATENT DOCUMENTS

| | | | |
|---|---|---|---|
| 2,640,082 | 5/1953 | Schreyer | 564/473 |
| 3,177,258 | 4/1965 | Rylander et al. | 564/490 |
| 3,355,483 | 11/1967 | Dickey et al. | 260/488 |
| 3,584,045 | 6/1971 | Feldman et al. | 260/563 |
| 4,042,629 | 8/1977 | Kershaw | 564/490 |
| 4,100,111 | 7/1978 | Peter et al. | 528/116 |

FOREIGN PATENT DOCUMENTS

| | | |
|---|---|---|
| 2841585 | 3/1980 | European Pat. Off. |
| 0042119 | 12/1981 | European Pat. Off. |
| 2111765 | 9/1971 | Fed. Rep. of Germany |
| 1252427 | 11/1971 | United Kingdom |
| 1498998 | 1/1978 | United Kingdom |

OTHER PUBLICATIONS

C.R. Acad. Sc. Paris, Ser. C, 268, (1969) 1949–1952.

*Primary Examiner*—Richard L. Raymond
*Assistant Examiner*—Shailendra Kumar
*Attorney, Agent, or Firm*—John H. Shurtleff

[57] ABSTRACT

A process for the preparation of a 2,2-disubstituted pentane-1,5-diamine of the formula I

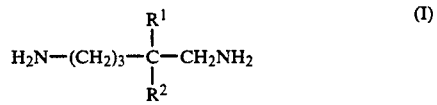

where $R^1$ and $R^2$, independently of one another, are $C_1$- to $C_{10}$-alkyl or $C_2$- to $C_{10}$-alkenyl or together are a $C_4$- to $C_7$-alkylene chain which is unsubstituted or monosubstituted to pentasubstituted by $C_1$- to $C_4$-alkyl, from a 2,2-disubstituted 4-cyanobutanal of the formula II

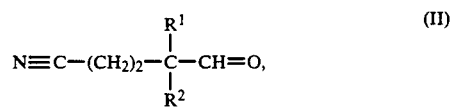

where $R^1$ and $R^2$ are as defined above, comprises, in two spatially separate reaction spaces,
  a) reacting the 4-cyanobutanal of the formula II, in a first reaction space, with excess ammonia on an acidic heterogeneous catalyst at from 20° to 150° C. and at from 15 to 500 bar, and
  b) hydrogenating the resultant reaction product, in a second reaction space, using excess hydrogen in the presence of excess ammonia on a catalyst containing cobalt, nickel, ruthenium and/or another noble metal, if desired with a basic component or on a basic or neutral carrier, at from 60° to 150° C. and at from 50 to 500 bar.

16 Claims, No Drawings

PREPARATION OF 2,2-DISUBSTITUTED PENTANE-1,5-DIAMINES

The present invention relates to a novel process for the preparation of 2,2-disubstituted pentane-1,5-diamines from 2,2-disubstituted 4-cyanobutanals.

C.R. Acad. Sci., Paris, Ser. C 268 (1969), 1949–1952, describes the preparation of 2,2-dimethylpentane-1,5-diamine from 4-cyano-2,2-dimethylbutanal and from 2,2-dimethylglutaronitrile. This aminative hydrogenation of 4-cyano-2,2-dimethylbutanal in ethanol in the presence of Raney cobalt at 650 bar gives 2,2-dimethylpentane-1,5-diamine in a yield of 34%. The 2,2-dimethylglutaronitrile, prepared by a complex route by reacting 4-cyano-2,2-dimethylbutanal with hydroxylamine and dehydrating the product, was converted into 2,2-dimethylpentane-1,5-diamine in a yield of 70% in ethanol at a pressure of 200 bar. For industrial utilization of the process, the yield in the aminative hydrogenation of 4-cyano-2,2-dimethylbutanal is inadequate. In addition, the reaction requires a pressure of 650 bar and the use of the solvent ethanol. The preparation of 2,2-dimethylpentane-1,5-diamine from the corresponding dinitrile on an industrial scale fails in particular due to the inaccessibility of the starting material.

DE-A-21 11 765 describes a process for the preparation of piperidines in which an N-substituted 4-cyanoaldimine is hydrogenated, forming a C-substituted piperidine and a primary amine, to the nitrogen atom of which the same substituent is bonded "as to the nitrogen atom of the aldimine". As byproducts, as can be seen from page 3, lines 3 to 6, small amounts of 1,5-diamines are produced. Thus, according to Examples 1 and 2, hydrogenation of N-cyclohexyl-4-cyano-2,2-dimethylbutyraldimine on Raney nickel at 120° C. and at from 55 to 60 bar gives from 6 to 7% of 2,2-dimethylpentane-1,5-diamine, and, according to Example 5, a similar reaction of N-cyclohexyl-4-cyano-2-ethylbutyraldimine gives 4% of 2-ethylpentane-1,5-diamine.

DE-A-28 41 585 describes a process for the preparation of 2,2-dialkylpentane-1,5-diamines in which, in a first step, a 4-cyano-2,2-dialkylbutanal is reacted with hydrogen and ammonia at from 50 to 250 bar and at from 80° to 160° C. in the presence of a group 8 metal as catalyst, to give the azomethine of 4-cyano-2,2-dialkylbutanal and 4-cyano-2,2-dialkylbutylamine, and, in a second step, said azomethine is reacted with hydrogen and ammonia at from 50 to 500 bar and at from 50° to 250° C. in the presence of a cobalt catalyst. As can be seen from Examples 1 to 4, this reaction proceeds in unsatisfactory yield and space-time yield for 4-cyano-2,2-dimethylbutanal (step 1: yield 66.8%, step 2 yield 65.2%, overall yield: 43.5%). For 4-cyano-2,2-diethylbutanal and 4-cyano-2-n-butyl-2-ethylbutanal, the yields for the first step drop to 46.4% (Example 2) and 57.5% (Example 3) respectively. The hydrogenation of the azomethines prepared from 4-cyano-2,2-diethyl- and 4-cyano-2-n-butyl-2-ethylbutanal is not described.

Finally, EP-A-42 119 describes a process for the preparation of primary monoamines and diamines from oxo compounds, which may, if desired, also contain other groups which are capable of reduction, using ammonia and hydrogen in the presence of a known hydrogenation catalyst, in which the reaction with ammonia and hydrogen in the presence of a hydrogenation catalyst is preceded by pre-reacting the oxo compound with ammonia at from 10 to 200° C. and at from 1 to 300 bar in the presence of an inorganic or organic ion exchanger in the ammonium form as imination catalyst. The use of the process is described in the examples exclusively for the aminative hydrogenation of 3-cyano-3,5,5-trimethylcyclohexanone (isophorone nitrile) and 2,2,6,6-tetramethyl-4-piperidone (triacetoneamine). In the aminative hydrogenation of isophorone nitrile, the use of the organic ion exchanger Lewatit SP ® 120 in the imination achieves a slight improvement in yield compared with the uncatalyzed procedure (cf. Comparative Example 3 in EP-A-42 119: yield 90.3%, with Lewatit SP ® 120: 93.9 to 94.7%).

Thus, there was hitherto no process available by which 4-cyano-2-ethylbutanal and 4-cyano-2,2-dimethylbutanal can be converted into the corresponding diamines under industrially practicable conditions and in economically satisfactory yields. Pentane-2,5-diamines having a relatively high degree of alkylation were hitherto unknown.

It is therefore an object of the present invention to provide a process which permits industrially and economically satisfactory access to 2,2-disubstituted pentane-1,5-diamines from 4-cyanobutanals and thus also the preparation of novel pentane-1,5-diamines having a relatively high degree of substitution in the 2-position.

We have found that this object is achieved by a novel and improved process for the preparation of a 2,2-disubstituted pentane-1,5-diamine of the formula I

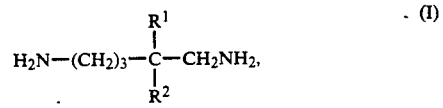

where $R^1$ and $R^2$, independently of one another, are $C_1$- to $C_{10}$-alkyl or $C_2$- to $C_{10}$-alkenyl or together are a $C_4$- to $C_7$-alkylene chain which is unsubstituted or monosubstituted to pentasubstituted by $C_1$- to $C_4$-alkyl, from a 2,2-disubstituted 4-cyanobutanal of the formula II

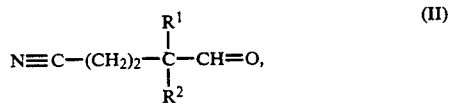

where $R^1$ and $R^2$, are as defined above, which comprises, in two spatially separate reaction spaces, a) reacting the 4-cyanobutanal of the formula II, in a first reaction space, with excess ammonia on an acidic heterogeneous catalyst at from 20° to 150° C. and at from 15 to 500 bar, and b) hydrogenating the resultant reaction product, in a second reaction space, using excess hydrogen in the presence of excess ammonia on a catalyst containing cobalt, nickel, ruthenium and/or another noble metal, if desired with a basic component or on a basic or neutral carrier, at from 60° to 150° C. and at from 50 to 500 bar.

The present invention furthermore provides novel 2,2-disubstituted pentane-1,5-diamines of the formula I'

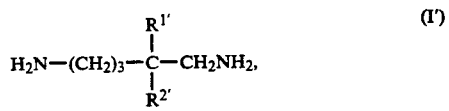

where $R^{1'}$ and $R^{2'}$, independently of one another, are $C_1$- to $C_4$-alkyl or $C_2$- to $C_{10}$-alkenyl or together are a $C_4$- to $C_7$-alkylene chain which is unsubstituted or monosubstituted to pentasubstituted by $C_1$- to $C_4$-alkyl, with the proviso that $R^{1'}$ and $R^{2'}$ are not simultaneously methyl.

The process according to the invention can be carried out as follows in two spatially separate reaction spaces:

a) In a first process step, a 2,2-disubstituted 4-cyanobutanal is reacted with excess ammonia while a pressure of from 15 to 500 bar, preferably from 100 to 350 bar, and a temperature of from 20 to 150° C., preferably from 30° to 100° C., are maintained. The condensation is carried out in the presence of an acidic heterogeneous catalyst, such as a metal compound having a Lewis acid or Brönstedt acid character, eg. alumina, silica, titanium dioxide or zirconium dioxide, and furthermore phosphates, eg. aluminum phosphates, or silicates, eg. amorphous or crystalline aluminosilicates. Preference is given to alumina, titanium dioxide, zirconium dioxide and silica, in particular alumina and titanium dioxide The acidity of the catalyst may be increased, if necessary, by doping with a halide. Thus, for example, halogen-doped catalysts, such as chloride on alumina or chloride on titanium dioxide, are also used.

In the reaction of the 2,2-disubstituted 4-cyanobutanal on the acidic heterogeneous catalyst, a weight hourly space velocity of from 0.01 to 10, preferably from 0.05 to 7, particularly preferably from 0.1 to 5, kg of 2,2-disubstituted 4-cyanobutanal per kg of catalyst per hour is maintained. It is expedient, but not absolutely necessary, to employ from 5 to 500 mol, preferably from 10 to 400 mol, particularly preferably from 20 to 300 mol, of $NH_3$ per mol of 2,2-disubstituted 4-cyanobutanal. The reaction of 4-cyanobutanal with ammonia may also be carried out in the presence of an inert solvent, such as an alkanol or tetrahydrofuran.

The reaction of the 2,2-disubstituted 4-cyanobutanal can be carried out batchwise, but preferably continuously, for example in a pressurized reactor or in a pressurized reactor cascade. In a particularly preferred embodiment, the 2,2-disubstituted 4-cyanobutanal and $NH_3$ are passed through a tubular reactor in which the catalyst is arranged in the form of a fixed bed.

The overall residence time in step 1 is given by the weight hourly space velocity and the amount of ammonia employed, and is expediently in the range from 0.5 to 120 minutes, preferably from 1 to 40 minutes, particularly preferably from 1.5 to 20 minutes.

b) The product obtained is fed to a second process step, a catalytic hydrogenation, together with from 3 to 10,000 mole equivalents, preferably from 4.5 to 30 mole equivalents, of hydrogen, if desired after introduction of further ammonia The hydrogenation is preferably carried out in liquid ammonia. From 5 to 500 mol, preferably from 10 to 400 mol, particularly preferably from 20 to 300 mol, of $NH_3$ are used per mol of 2,2-disubstituted 3-cyanobutanal employed in step 1. The proportion of $NH_3$ may, if desired, be increased to the desired level by feeding in $NH_3$.

The hydrogenation is generally carried out at from 60° to 150° C., preferably from 70° to 140° C., particularly preferably from 80° to 130° C., and at from 50 to 500 bar, particularly from 100 to 350 bar, particularly preferably from 150 to 300 bar.

The weight hourly space velocity is expediently in the range from 0.01 to 5 kg/[kg.h], preferably from 0.02 to 2.5 kg/[kg.h], particularly preferably from 0.05 to 2 kg/[kg.h].

In the case of continuous hydrogenation without product recycling, the overall residence time is given by the weight hourly space velocity and the amount of ammonia employed, and is in the range from 0.5 to 120 minutes, preferably from 1 to 40 minutes, particularly preferably from 1.5 to 20 minutes.

Any conventional hydrogenation catalyst which contains nickel, cobalt, iron, copper, ruthenium or another sub-group VIII noble metal can in principle be employed in the hydrogenation. Preference is given to ruthenium, cobalt or nickel catalysts. Particular preference is given to ruthenium and cobalt catalysts. The catalytically active metal may be employed in supported or unsupported form. Examples of suitable carriers are alumina, titanium dioxide, zirconium dioxide, zinc oxide or magnesium oxide/alumina, but hydrogenation catalysts with basic components, such as oxides and hydroxides of alkali and alkaline earth metals are preferred. Particular preference is therefore given to basic carriers, eg. $\beta$-alumina or magnesium oxide/aluminas. Particular preference is given to magnesium oxide/alumina containing from 5 to 40% of magnesium oxide. The carrier containing magnesium oxide and aluminas may be amorphous or in the form of spinel.

The basic component may also be added, if desired, during the hydrogenation process, eg. as a solution of an alkali metal hydroxide or alkaline earth metal hydroxide in water.

Particular preference is given in the hydrogenation to cobalt or ruthenium with a basic component. These catalysts are obtained industrially in a conventional manner; for example, ruthenium on a basic carrier is obtained by applying an aqueous ruthenium salt solution such as ruthenium chloride or ruthenium nitrate, to the appropriate carrier. The ruthenium concentration on the carrier is from 0.1 to 10%, preferably from 0.5 to 5%, particularly preferably from 1 to 4%.

After drying and possibly after calcination at from 120° to 500° C., preferably at from 200° to 400° C., the ruthenium catalyst is activated in a stream of hydrogen at from 180° to 250° C., preferably at from 190° to 230° C., and at from 1 to 500 bar, preferably at from 20 to 300 bar, for from 1 to 20 hours, preferably for from 2 to 10 hours.

The ruthenium catalyst may, if desired, contain further metals, eg. palladium or iron. The iron content is generally in the range from 0.5 to 5%, and the palladium content in the range from 0.1 to 5%.

The reaction is preferably carried out continuously, eg. in a pressure-tight stirred reactor or in a stirred reactor cascade. In a particularly preferred embodiment, a tubular reactor is employed in which the hydrogenation mixture is passed over a fixed catalyst bed using the pool or trickle method.

Process steps a and b may likewise be carried out in a single reactor in which the imination catalyst and the hydrogenation catalyst are arranged in two separate layers. In this case, the imination is expediently carried out in the presence of hydrogen.

After the hydrogenation, any excess ammonia is removed under pressure. The 2,2-disubstituted pentane-1,5-diamine obtained in this way (eg. 2,2-dimethylpentane-1,5-diamine from 4-cyano-2,2-dimethylbutanal, 2-methyl-2-propylpentane-1,5-diamine from 4-cyano-2-methyl-2-propylbutanal or 2-n-butyl-2-ethylpentane-1,5-diamine from 4-cyano-2-butyl-2-ethylbutanal) can be isolated by fractional distillation. 3-Substituted piperidines (eg. 3,3-dimethylpiperidine from 4-cyano-2-methyl-2-propylbutanal or 3-butyl-3-ethylpiperidine from 4-cyano-2-butyl-2-ethylbutanal) are only formed to a minor extent as a byproduct.

The starting materials for the process, the 2,2-disubstituted 4-cyanobutanals, are accessible from 2,2-disubstituted aldehydes- and acrylonitrile. The process according to the invention makes it possible for the first time to convert a 2,2-disubstituted 4-cyanobutanal into the 2,2-disubstituted pentane-1,5-diamine in high yield and high space-time yield.

$R^1$ and $R^2$ in the compounds I and II have the following meanings:

$R^1$ and $R^2$, independently of one another, are $C_1$- to $C_{10}$-alkyl, preferably $C_1$- to $C_8$-alkyl, particularly preferably $C_1$- to $C_4$-alkyl, such as methyl, ethyl, n-propyl, isopropyl, n-butyl, isobutyl, sec-butyl or tert-butyl, $C_2$- to $C_{10}$-alkenyl, preferably $C_2$- to $C_8$-alkenyl, particularly preferably $C_2$- to $C_4$-alkenyl, such as allyl or 1-butenyl, together are a $C_4$- to $C_7$-alkylene chain which is unsubstituted or monosubstituted to pentasubstituted by $C_1$- to $C_4$-alkyl, such as $—(CH_2)_4—$, $—(CH_2)_5—$, $—(CH_2)_6—$, $—(CH_2)_7—$ or $—CH(CH_3)—(CH_2)_3—$.

Examples of preferred 2,2-disubstituted 4-cyanobutanals of the formula II are 2,2-dimethyl-4-cyanobutanal, 2-methyl-2-propenyl-4-cyanobutanal, 2-ethyl2-butenyl-4-cyanobutanal, 2-methyl-2-propyl-4-cyanobutanal, 2-ethyl-2-butyl-4-cyanobutanal, 2-methyl-2-nonyl-4-cyanobutanal, 1-cyanoethylcyclohexanecarboxaldehyde and 1-cyanoethylcyclopentanecarboxaldehyde. These starting materials are readily accessible from isobutyraldehyde, 2-methylpentanal, 2-methylpentanal, 2-ethylhexanal, 2-ethylhexanal, 2-methylundecanal, cyclohexanecarboxaldehyde. and cyclopentanecarboxaldehyde. Preferred 2,2-disubstituted pentane-1,5-diamines of the formula I are 2,2-dimethylpentane-1,5-diamine, 2-methyl-2-propylpentane-1,5-diamine, 2-methyl-2-propenylpentane-1,5-diamine, 2-ethyl-2-n-butyl-pentane-1,5-diamine, 2-ethyl-2-n-butenylpentane-1,5-diamine, 2-methyl-2-nonylpentane-1,5-diamine, 1-(3-aminopropyl)-1-aminomephylcyclohexane and 1-(3-aminopropyl-)-1-aminomethylcyclopentane.

$R^{1'}$ and $R^{2'}$ in the compounds I' have the following meanings:

$R^{1'}$ and $R^{2'}$, independently of one another, are $C_1$- to $C_{10}$-alkyl, preferably $C_1$- to $C_8$-alkyl, particularly preferably $C_1$- to $C_4$-alkyl, such as methyl, ethyl, n-propyl, isopropyl, n-butyl, isobutyl, sec-butyl or tert-butyl, with the proviso that $R^{1'}$ and $R^{2'}$ are not simultaneously methyl, $C_2$- to $C_{10}$-alkenyl, preferably $C_2$- to $C_8$-alkenyl, particularly preferably $C_2$- to $C_4$-alkenyl, such as allyl or butenyl, together are a $C_4$- to $C_7$-alkylene chain which is unsubstituted or monosubstituted to pentasubstituted by $C_1$- to $C_4$-alkyl, such as $—(CH_2)_4—$, $—(CH_2)_5—$, $—(CH_2)_6—$, $—(CH_2)_7—$ or $—CH(CH_3)—(CH_2)_3—$.

Preferred compounds I' are:

2,2-dimethylpentane-1,5-diamine
2-ethyl-2-methylpentane-1,5-diamine
2-methyl-2-n-propylpentane-1,5-diamine
2-n-butyl-2-ethylpentane-1,5-diamine
2-methyl-2-n-nonylpentane-1,5-diamine
2-methyl-2-n-propenylpentane-1,5-diamine
2-n-butenyl-2-ethylpentane-1,5-diamine
2-n-pentyl-2-propylpentane-1,5-diamine
2-n-pentenyl-2-propylpentane-1,5-diamine
1-(3-aminopropyl)-1-aminomethyl oyclohexane
1-(3-aminopropyl)-1-aminomethyl cyclopentane The diamines claimed have lower volatility and greater asymmetry (various reactivity of the amine functions) than the known alkylpentanediamines, such as 2-methyl- and 2,2-dimethylpentanediamine, as a consequence of the greater degree of substitution. This results, inter alia, in better processing properties of the diamines, e.g., as components curing agents for epoxides and components for nylons, and lower odor nuisance caused by unreacted diamines and the diisocyanates which can be prepared therefrom.

EXAMPLES

Example 1

A vertical tubular reactor (diameter 16 mm, fill level 50 cm, oil-heated twin jacket) was filled with 81.9 g (93 ml) of a catalyst containing 3% of ruthenium on a magnesium oxide/alumina carrier (10% of MgO, 90% of $Al_2O_3$) in the form of 1 to 1.5 mm grit (catalyst preparation by impregnating the pores of a magnesium oxide/alumina carrier with an aqueous ruthenium nitrate solution and drying the catalyst at 120° C.). The reduction was carried out at 100 bar while simultaneously passing 100 l(S.T.P.)/h of hydrogen through the catalyst, which was kept at 220° C. for 7 hours after increasing the temperature in steps from 100° to 220° C. over the course of 6 hours.

34.0 g per hour of 2,2-dimethyl-4-cyanobutanal (purity 93.4%, 31.8 g, 0.254 mol) and 1450 ml (870 g, 51.1 mol) per hour of liquid ammonia were pumped at 250 bar and 60° C. through a tubular reactor (diameter 16 mm, fill level 50 cm, oil-heated twin jacket) upstream of the hydrogenation reactor and filled with 63.5 g (100 ml) of $TiO_2$ (anatase) in the form of 1.5 mm pellets. The discharge from the reactor was subsequently passed through the hydrogenation reactor from bottom to top at 250 bar and 120° C. while simultaneously passing 100 l (S.T.P.)/h (4.5 mol) of hydrogen through the reactor. The product stream was decompressed to atmospheric pressure and $NH_3$ was removed by distillation. The product from 32.4 hours was separated by fractional distillation on a 30 cm packed column (3 mm glass rings), giving 344.8 g of 3,3-dimethylpiperidine (b.p. 50°–52° C./210 mmHg) and 753.6 g of 2,2-dimethylpentane-1,5-diamine (b.p.=72° C./8 mmHg). The diamine yield was 70.5% of theory.

Example 2

Example 1 was repeated using 2-methyl-2-propyl-4-cyanobutanal as the starting material. 33.5 g per hour of 2-methyl-2-propyl-4-cyanobutanal (purity 88.9%, 29.8 g, 0.195 mol) and 1400 ml (840 g, 49.4 mol) per hour of liquid ammonia were pumped at 250 bar and 60° C. through the imination reactor. The product stream was subsequently passed through the hydrogenation reactor from bottom to top at 250 bar and 120° C. while simultaneously passing 100 l(S.T.P.)/h (4.5 mol) of hydrogen through the reactor. The product stream was decompressed to atmospheric pressure and $NH_3$ was removed by distillation. The product from 37.5 hours was separated by fractional distillation on a 30 cm packed column (3 mm glass rings), giving 277.0 g of 3-methyl-3-propylpiperidine (b.p.=46° C./2 mmHg) and 842.1 g of 2-methyl-2-propylpentane-1,5-diamine (b.p.=78°-81° C./2 mmHg). The diamine yield was 72.9% of theory.

Example 3

Example 2 was repeated, with 55.9 g of 2-methyl-2-propyl-4-cyanobutanal (purity 86.6%, 48.4 g, 0.316 mol) per hour and 1365 ml (819 g, 48.2 mol) per hour of liquid ammonia at 250 bar and 60° C. being pumped through the imination reactor. The product stream was subsequently passed through the hydrogenation reactor from bottom to top at 250 bar and 120° C. while simultaneously passing 100 l(S.T.P.)/h (4.5 mol) of hydrogen through the reactor. The product stream was decompressed to atmospheric pressure and NH3 was removed by distillation. The product from 16.8 hours was separated by fractional distillation on a 30 cm packed column (3 mm glass rings), giving 174.4 g of 3-methyl-3-propylpiperidine and 501.6 g of 2-methyl-2-propylpentane-1,5-diamine. The diamine yield was 59.6% of theory.

Example 4

Example 3 was repeated, with 78.5 g per hour of 2-methyl-2-propyl-4-cyanobutanal (purity 86.6%, 68.0 g, 0.444 mol) and 1340 ml (804 g, 47.3 mol) per hour of liquid ammonia at 250 bar and 60° C. being pumped through the imination reactor. The product stream was subsequently passed through the hydrogenation reactor from bottom to top at 250 bar and 120° C. while simultaneously passing 150 l(S.T.P.)/h (6.7 mol) of hydrogen through the reactor. The product stream was decompressed to atmospheric pressure and NH: was removed by distillation. The product from 4.2 hours was separated by fractional distillation on a 30 cm packed column (3 mm glass rings), giving 96.0 g of 3-methyl-3-propylpiperidine and 162.8 g of 2-methyl-2-propylpentane-1,5-diamine. The diamine yield was 55.1% of theory.

Example 5

Example 1 was repeated using 2-butyl-2-ethyl-4-cyanobutanal as the starting material. To this end, 33.6 g per hour of 2-butyl-2-ethyl-4-cyanobutanal (purity 89.0%, 29.9 g, 0.165 mol) and 1344 ml (806 g, 47.4 mol) per hour of liquid ammonia were pumped at 250 bar and 60° C. through the imination reactor. The product stream was subsequently passed through the hydrogenation reactor from bottom to top at 250 bar and 120° C. while simultaneously passing 100 l(S.T.P.)/h (4.5 mol) of hydrogen through the reactor. The product stream was decompressed to atmospheric pressure and NH3 was removed by distillation. The product from 16.7 hours was separated by fractional distillation on a 30 cm packed column (3 mm glass rings), giving 166.8 g of 3-butyl-3-ethylpiperidine (b.p.=73° to 75° C./2 mmHg) and 267.5 g of 2-butyl-2-ethylpentane-1,5-diamine (b.p.=105° C./2 mmHg). The diamine yield was 52.1% of theory.

Example 6

A vertical tubular reactor (diameter 16 mm, fill level 50 cm, oil-heated twin jacket) was filled with 90.1 g (87 ml) of a catalyst containing 3% of ruthenium on β-alumina in the form of 1.2 mm pellets (catalyst preparation by impregnating the pores of β-alumina with aqueous ruthenium nitrate solution and drying the catalyst at 120° C.). The reduction was carried out at 100 bar while simultaneously passing 150 l(S.T.P.)/h of hydrogen through the catalyst, which was kept at 220° C. for 9 hours after increasing the temperature in steps from 100° to 220° C. over the course of 7 hours.

41.6 g per hour of 2-butyl-2-ethyl-4-cyanobutanal (purity 90%, 37.4 g, 0.207 mol) and 1073 ml (646 g, 38.0 mol) per hour of liquid ammonia were pumped at 250 bar and 50° C. through a tubular reactor (diameter 16 mm, fill level 50 cm, oil-heated twin jacket) upstream of the hydrogenation reactor and filled with 43.3 g (96 ml) of a Y-zeolite pelleted with Aerosil 200 (HY-zeolite: Aerosil 200 =9:1, SiO2:Al2O3=6:1). The product stream was subsequently passed through the hydrogenation reactor from bottom to top at 250 bar and 120° C. while simultaneously passing 80 l(S.T.P.)/h (3.6 mol) of hydrogen through the reactor. The product stream was decompressed to atmospheric pressure and NH3 was removed by distillation. The product from 34.1 hours was separated by fractional distillation on a 30 cm packed column (3 mm glass rings), giving 358.3 g of 3-butyl-3-ethylpiperidine and 747.7 g of 2-butyl-2-ethylpentane-1,5-diamine. The diamine yield was 56.9% of theory.

Example 7

A vertical tubular reactor (diameter 16 mm, fill level 50 cm, oil-heated twin jacket) was filled with 90.1 g (87 ml) of a catalyst containing 3% of ruthenium on β-alumina in the form of 1.2 mm pellets (catalyst preparation by impregnating the pores of β-alumina with aqueous ruthenium nitrate solution and drying the catalyst at 120° C.). The reduction was carried out at 100 bar while simultaneously passing 150 l(S.T.P.)/h of hydrogen through the catalyst, which was kept at 220° C. for 9 hours after increasing the temperature in steps from 100 to 220° C. over the course of 7 hours.

45.1 g per hour of 2-butenyl-2-ethyl-4-cyanobutanal (purity 64.0%, 28.9 g, 0.161 mol) and 950 ml (570 g, 33.5 mol) per hour of liquid ammonia were pumped at 250 bar and 50° C. through a tubular reactor (diameter 16 mm, fill level 50 cm, oil-heated twin jacket) upstream of the hydrogenation reactor and filled with 43.3 g (96 ml) of a Y-zeolite pelleted with Aerosil 200 (HY-zeolite: Aerosil 200=9:1, SiO2:Al2O3=6:1). The product stream was subsequently passed through the hydrogenation reactor from bottom to top at 250 bar and 120° C. while simultaneously passing 100 l(S.T.P.)/h (4.5 mol) of hydrogen through the reactor. The product stream was decompressed to atmospheric pressure and NH3 was removed by distillation. From the product from 23.9 hours, 205.7 g of 3-butyl-3-ethylpiperidine and 438.4 g of a mixture of 2-butyl- and 2-butenyl-2-ethylpentane-1,5-diamine (8:1), corresponding to a diamine yield of 61.9% of theory, were isolated by fractional distillation on a 30 cm packed column (3 mm glass rings).

Example 8

A vertical tubular reactor (diameter 16 mm, fill level 50 cm, oil-heated twin jacket) was filled with 183.1 g (100 ml) of an unsupported cobalt catalyst (composition: CoO with 5% of Mn3O4 and 3% of P2O5) in the form of 1 to 1.5 mm grit. The reduction was carried out at 100 bar while simultaneously passing 150 l(S.T.P.)/h of hydrogen through the catalyst, which was kept at 330° C. for 30 hours after increasing the temperature in steps from 100° to 330° C. over the course of 23 hours.

10.8 g per hour of 2-butyl-2-ethyl-4-cyanobutanal (purity 98.2%, 9.3 g, 0.052 mol) and 478 ml (287 g, 16.9 mol) per hour of liquid ammonia were pumped at 200 bar and 80° C. through a tubular reactor (diameter 16 mm, fill level 50 cm, oil-heated twin jacket) upstream of the hydrogenation reactor and filled with 63.5 g (100 ml) of TiO2 (anatase) in the form of 1.5 mm pellets. The product stream was subsequently passed through the hydrogenation reactor from bottom to top at 200 bar and 110° C. while simultaneously passing 60 l(S.T.P.)/h (2.7 mol) of hydrogen through the reactor. The product stream was decompressed to atmospheric pressure and NH3 was removed by distillation. According to GC, the hydrogenation product stream contained 67.2% of 2-butyl-2-ethylpentane-1,5-diamine and 24.7% of 3-butyl-3-ethylpiperidine, corresponding to a diamine yield of 66.2% of theory.

Example 9

A vertical tubular reactor (diameter 16 mm, fill level 100 cm, oil-heated twin jacket) was filled with 354 g (200 ml) of a basic unsupported cobalt catalyst (CoO containing 5% of Mn2O3 and 1.4% of Na2O) in the form of 1 to 1.5 mm grit. The catalyst was reduced at 100 bar while simultaneously passing 150 l(S.T.P.)/h of hydrogen through the catalyst, which was kept at 330° C. for 30 hours after increasing the temperature in steps from 100° to 330° C. over the course of 23 hours.

80.0 g per hour of 2-butyl-2-ethyl-4-cyanobutanal (purity 99.3%, 0.44 mol) and 200 g (330 ml, 11.76 mol) per hour of liquid ammonia were pumped from bottom to top at 250 bar and 80° C. through a tubular reactor (diameter 16 mm, fill level 20 cm, oil-heated twin jacket) upstream of the hydrogenation reactor and filled with 25.4 g (40 ml) of TiO2 (anatase) in the form of 1.5 mm pellets. 100 l(S.T.P.)/h of hydrogen were then fed in, and the product stream from the upstream imination reactor was passed through the hydrogenation reactor from bottom to top at 250 bar and 110° C. The product stream was decompressed to atmospheric pressure and the ammonia was removed by distillation. According to gas-chromatographic analysis, the hydrogenation product stream contained 89.2% of 2-butyl-2-ethylpentane-1,5-diamine and 4.3% of 3-butyl-3-ethylpiperidine. The product from 80.5 hours was separated by fractional distillation on a 30 cm packed column (3 mm glass rings), giving 5738 g of 2-butyl-2-ethylpentane-1,5-diamine, corresponding to a yield of 87.3% of theory.

Example 10

A vertical tubular reactor (diameter 16 mm, fill level 50 cm, oil-heated twin jacket) was filled with 176.7 g (100 ml) of a basic unsupported cobalt catalyst (CoO containing 5% of Mn2O3 and 1.4% of Na2O) in the form of 1 to 1.5 mm grit. The catalyst was reduced at 100 bar while simultaneously passing 150 l(S.T.P.)/h of hydrogen through the catalyst, which was kept at 330° C. for 30 hours after increasing the temperature in steps from 100° to 330° C. over the course of 23 hours.

20.0 g per hour of 2-butyl-2-ethyl-4-cyanobutanal (purity 99.3%, 0.11 mol) and 140 g (230 ml, 8.23 mol) per hour of liquid ammonia were pumped from bottom to top at 250 bar and 80° C. through a tubular reactor (diameter 16 mm, fill level 50 cm, oil-heated twin jacket) upstream of the hydrogenation reactor and filled with 70.0 g (100 ml) of $\gamma$-Al2O3 in the form of 1.5 mm pellets. 60 l(S.T.P.)/h of hydrogen were then fed in, and the product stream from the upstream imination reactor was passed through the hydrogenation reactor from bottom to top at 250 bar and 110° C. The product stream was decompressed to atmospheric pressure and the ammonia was removed by distillation. According to gas-chromatographic analysis, the hydrogenation product stream contained 95.4% of 2-butyl-2-ethylpentane-1,5-diamine and 2.3% of 3-butyl-3-ethylpiperidine. The product from 48.0 hours was separated by fractional distillation on a 30 cm packed column (3 mm glass rings), giving 920 g of 2-butyl-2-ethylpentane-1,5-diamine, corresponding to a yield of 93.9% of theory.

We claim:

1. A process for the preparation of 2,2-disubstituted pentane-1,5-diamine of the formula

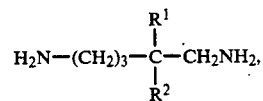

$$H_2N-(CH_2)_3-\underset{\underset{R^2}{|}}{\overset{\overset{R^1}{|}}{C}}-CH_2NH_2, \qquad I$$

where $R^1$ and $R^2$, independently of one another, are $C_1$- to $C_{10}$-alkyl or $C_2$- $C_{10}$-alkenyl or together are a $C_4$- to $C_7$-alkylene chain which is unsubstituted or monosubstituted to pentasubstituted by $C_1$- to $C_4$-alkyl, from a 2,2-disubstituted 4-cyanobutanal of the formula II

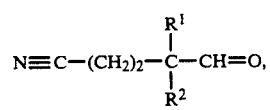

$$N\equiv C-(CH_2)_2-\underset{\underset{R^2}{|}}{\overset{\overset{R^1}{|}}{C}}-CH=O, \qquad II$$

where $R^1$ and $R^2$ are as defined above, which comprises, in two spatially separate reaction spaces, a) reacting the 4-cyanobutanal of the formula II, in a first reaction space, with excess ammonia on an acidic heterogeneous catalyst selected from the group consisting of alumina, silica, titanium dioxide, zirconium dioxide, aluminum phosphates and amorphous or crystalline aluminasilicates, as the sole catalyst at a temperature of from 20° to 150° C. and a pressure of from 15 to 500 bar, and b) hydrogenating the resultant reaction product, in a second reaction space, using hydrogen in the presence of excess ammonia on a catalyst containing at least one member selected from the group consisting of cobalt, nickel and the noble metals of subgroup VIII of the Periodic Table at a temperature of from 60°0 to 150° C. and a pressure of from 50 to 500 bar.

2. A process as claimed in claim 1, wherein the acidic heterogeneous catalyst in said first reaction space is selected from the group consisting of alumina, titanium dioxide, zirconium dioxide and silica.

3. A process as claimed in claim 2, wherein the acidic heterogeneous catalyst is selected from the group consisting of alumina and titanium dioxide which has been doped with halogen to increase the acidity of the catalyst.

4. A process as claimed in claim 1, wherein the first reaction space has a temperature of from 30° to 100° C. and a pressure of from 100 to 350 bar, and the second reaction space has a temperature of from 70° to 140° C. and a pressure of from 100 to 350 bar.

5. A process as claimed in claim 4, wherein the second reaction space has a temperature of from 80° to 130° C. and a pressure of from 150 to 300 bar.

6. A process as claimed in claim 1, wherein the ammonia is used in the first reaction space in an excess amount of from 5 to 500 mols per mol of 2,2-disubstituted-4-cyanobutanol.

7. A process as claimed in claim 6, wherein the excess amount of ammonia is from 10 to 400 mols per mol of 2,2-disubstituted-3-cyanobutanol.

8. A process as claimed in claim 6, wherein the excess amount of ammonia is from 20 to 300 mols per mol of 2,2-disubstituted-3-cyanobutanol.

9. A process as claimed in claim 1, wherein the hydrogenation catalyst in the second reaction space contains at least one member selected from the group consisting of nickel, cobalt and ruthenium.

10. A process as claimed in claim 1, wherein a ruthenium catalyst is used in the second reaction space.

11. A process as claimed in claim 1, wherein a cobalt catalyst is used in the second reaction space.

12. A process as claimed in claim 1, wherein the catalyst used in the hydrogenation reaction in the second reaction space is supported on a neutral to basic carrier.

13. A process as claimed in claim 12, wherein a cobalt or ruthenium hydrogenation catalyst is used.

14. A process as claimed in claim 1, wherein the catalyst used in the hydrogenation reaction in the second reaction space is an unsupported catalyst containing a basic component selected from the group consisting of the oxides and hydroxides of alkali and alkaline earth metals.

15. A process as claimed in claim 14, wherein a cobalt or ruthenium hydrogenation catalyst is used.

16. A process as claimed in claim 15, wherein 2-butyl-2-ethyl-4-cyanobutanal is reacted in said first and second reaction spaces to produce 2-butyl-2-ethylpentane-1,5-diamine.

* * * * *

UNITED STATES PATENT AND TRADEMARK OFFICE
CERTIFICATE OF CORRECTION

PATENT NO. : 5,166,443
DATED : November 24, 1992
INVENTOR(S) : Merger et al

It is certified that error appears in the above-identified patent and that said Letters Patent is hereby corrected as shown below:

ON THE FRONT PAGE:

The Filing Date should be changed from "Mar. 17, 1991" to read

--Mar. 27, 1991--.

IN THE CLAIMS:

In Claim 6, line 4: change "cyanobutanol" to read

--cyanobutanal--.

Signed and Sealed this

Twelfth Day of October, 1993

Attest:

BRUCE LEHMAN

Attesting Officer

Commissioner of Patents and Trademarks